(12) United States Patent
Braxton et al.

(10) Patent No.: US 6,197,519 B1
(45) Date of Patent: Mar. 6, 2001

(54) PANCREAS-DERIVED SERPIN

(75) Inventors: Scott Michael Braxton, San Mateo; Craig G. Wilde, Sunnyvale; Dinh Diep, San Francisco, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/361,773

(22) Filed: Jul. 27, 1999

Related U.S. Application Data

(62) Division of application No. 08/977,771, filed on Nov. 25, 1997.

(51) Int. Cl.⁷ .............................. C12Q 1/68; C07K 15/26

(52) U.S. Cl. ................................................. 435/6; 530/350

(58) Field of Search ..................... 435/6, 91.2; 530/350

(56) References Cited

U.S. PATENT DOCUMENTS 6,013,448 * 1/2000 Braxton et al. ......................... 435/6

* cited by examiner

*Primary Examiner*—Eggerton A. Campbell
(74) *Attorney, Agent, or Firm*—Incyte Genomics, Inc.

(57) ABSTRACT

The present invention provides nucleotide and amino acid sequences that identify and encode a novel pancreas-derived serpin (PDS) expressed in human pancreas. The present invention also provides for antisense molecules to the nucleotide sequences which encode PDS, expression vectors for the production of purified PDS, antibodies capable of binding specifically to PDS, hybridization probes or oligonucleotides for the detection of PDS-encoding nucleotide sequences, genetically engineered host cells for the expression of PDS, diagnostic tests based on PDS-encoding nucleic acid molecules and a pharmaceutical composition containing PDS capable of binding specifically to a serine protease.

4 Claims, 8 Drawing Sheets

```
         9              18          27             36         45            54
5' ATG GAC ACA ATC TTC GNG TGG AGT CTT CTA TTG CTG TTT NGG GGN AGT CAA GCC
   Met Asp Thr Ile Phe Xxx Trp Ser Leu Leu Leu Leu Phe Xxx Gly Ser Gln Ala 63             72          81             90         99           108
   TCA AGA TGC TCA GCT CAA AAA AAT ACC GAA TTT GGA GTG GAT CTT TAT CAA GAG
   Ser Arg Cys Ser Ala Gln Lys Asn Thr Glu Phe Gly Val Asp Leu Tyr Gln Glu 117            126         135            144        153          162
   GTT TCC TCT CAT AAG GAC AAC ATT TTT NCA CCC CTT GGA ATA NCT TTG
   Val Ser Leu Ser His Lys Asp Asn Ile Ile Phe Xxx Pro Leu Gly Ile Xxx Leu 171            180         189            198        207          216
   GNT CTC GAG ATG GNA CAA CTG GGA GCC AAA GGA CAG CAG NAG NTA AGA
   Xxx Leu Glu Met Xxx Gln Leu Gly Ala Lys Gly Lys Ala Gln Xxx Xxx Arg 225            234         243            252        261          270
   CAA ACT TTA CAA CAA CAG GAA NCC TCA GCT GGG GAA GAA TTT CTT TGT NCT GAA
   Gln Thr Leu Gln Gln Gln Glu Xxx Ser Ala Gly Glu Glu Phe Leu Cys Xxx Glu 279            288         297            306        315          324
   GTC ATT TTC TCT CTG CCA TCT CAG AGA AAA AAC AAG AAT TTA CAT TTA ATC TTG
   Val Ile Phe Ser Leu Pro Ser Gln Arg Lys Asn Lys Asn Leu His Leu Ile Leu
```

FIGURE 1A

```
       333             342             351             360             369             378
CCA ATG CCC TCT ACC TNT CAA GAA GGA TTC ACT GTG AAA GAA CAG TAT CTC CAT
Pro Met Pro Ser Thr Xxx Gln Glu Gly Phe Thr Val Lys Glu Gln Tyr Leu His 387             396             405             414             423             432
GGC AAC AAG GAA TNT TTT CAG AGT GCT ATA AAA CTG GTG GAT TTT CAA GAT GCA
Gly Asn Lys Glu Xxx Phe Gln Ser Ala Ile Lys Leu Val Asp Phe Gln Asp Ala 441             450             459             468             477             486
AAG GCT TGT GCA GGG ATG ATA AGT ACC TGG GTA GAA AGA AAA ACA GAT GGA AAA
Lys Ala Cys Ala Gly Met Ile Ser Thr Trp Val Glu Arg Lys Thr Asp Gly Lys 495             504             513             522             531             540
ATT AAA GAC ATG TTT TCA GGG GAA TTT GGC CCT CTG ACT CGG CTT GTC CTG
Ile Lys Asp Met Phe Ser Gly Glu Phe Gly Pro Leu Thr Arg Leu Val Leu 549             558             567             576             585             594
GTG AAT GCT ATT TAT TTC AAA GGA GAT TGG AAA CAG AAA TTC AGA AAA GAG GAC
Val Asn Ala Ile Tyr Phe Lys Gly Asp Trp Lys Gln Lys Phe Arg Lys Glu Asp 603             612             621             630             639             648
ACA CAG CTG ATA AAT TTT ACT AAG AAA AAT GGT TCA ACT GTC AAA ATT CCA ATG
Thr Gln Leu Ile Asn Phe Thr Lys Lys Asn Gly Ser Thr Val Lys Ile Pro Met
```

FIGURE 1B

```
       657              666              675              684              693              702
ATG AAG GCT CTT CTG AGA ACA AAA TAT GGT TAT TTT TCT GAA TCT TCC CTG AAC
Met Lys Ala Leu Leu Arg Thr Lys Tyr Gly Tyr Phe Ser Glu Ser Ser Leu Asn 711              720              729              738              747              756
TAC CAA GTT TTA GAA TTG TCT TAC AAA GGT GAT GAA TTT AGC TTA ATT ATC ATA
Tyr Gln Val Leu Glu Leu Ser Tyr Lys Gly Asp Glu Phe Ser Leu Ile Ile Ile 765              774              783              792              801              810
CTT CCT GCA GAA GGT ATG GAT ATA GAA GAA GTG GAA AAA CTA ATT ACT GCT CAA
Leu Pro Ala Glu Gly Met Asp Ile Glu Glu Val Glu Lys Leu Ile Thr Ala Gln 819              828              837              846              855              864
CAA ATC CTA AAA TGG CTC TCT GAG ATG CAA GAA GAG GAA GTA GAA ATA AGC CTC
Gln Ile Leu Lys Trp Leu Ser Glu Met Gln Glu Glu Glu Val Glu Ile Ser Leu 873              882              891              900              909              918
CCT AGA TTT AAA GTA GAA CAA AAA GTA GAC TTC AAA GAC GTT TTG TTT TCT TTG
Pro Arg Phe Lys Val Glu Gln Lys Val Asp Phe Lys Asp Val Leu Phe Ser Leu 927              936              945              954              963              972
AAC ATA ACC GAG ATA TTT AGT GGT GGC TGC GAC CTT TCT GGA ATA ACA GAT TCT
Asn Ile Thr Glu Ile Phe Ser Gly Gly Cys Asp Leu Ser Gly Ile Thr Asp Ser
```

FIGURE 1C

```
         981             990             999            1008            1017           1026
TCT GAA GTG TAT GTT TCC CAA GTG ACG CAA AAA GTT TTC TTT GAG ATA AAT GAA
Ser Glu Val Tyr Val Ser Gln Val Thr Gln Lys Val Phe Phe Glu Ile Asn Glu 1035            1044            1053            1062            1071           1080
GAT GGT AGT GAA GCT GCA ACA TCA ACT GGC ATA CAC ATC CCT GTG ATC ATG AGT
Asp Gly Ser Glu Ala Ala Thr Ser Thr Gly Ile His Ile Pro Val Ile Met Ser 1089            1098            1107            1116            1125           1134
CTG GCT CAA AGC CAA TTT ATA GCA AAT CAT CCA TTT CTG TTT ATT ATG AAG CAT
Leu Ala Gln Ser Gln Phe Ile Ala Asn His Pro Phe Leu Phe Ile Met Lys His 1143            1152            1161            1170            1179           1188
AAC CCA ACA GAA TCA ATT CTG TTT ATG GGA AGA GTG ACA AAT CCT GAC ACC CAG
Asn Pro Thr Glu Ser Ile Leu Phe Met Gly Arg Val Thr Asn Pro Asp Thr Gln 1197            1206            1215
GAG ATA AAA GGA AGA GAT TTA GAT TCA 3'
Glu Ile Lys Gly Arg Asp Leu Asp Ser
```

FIGURE 1D

```
                                                    - - - - - - - - - - - - - - - - - - - - - - - - - A X X N X X F X  Majority
            |         |         |         |
            10        20        30
  1   M D X X - - - - - - - - - - - - - - - - - - - - - - - - - - - - - - -
  1   M D T I F W S L L L L F X G S Q A S R C S A Q K N T E F G        222689.ami
  1   M D V L - - - - - - - - - - - - - - - - - - A E A N G T F A     g464490.PTI6_HUMAN
  1   M - - - - - - - - - - - - - - - - - - - - - - - - - - - - -    g510193.RNSERPIN_1

X X L X X X X X X X X X X X N X X F X P X X X X X X L X M X X  Majority
            |         |         |         |
            40        50        60
 31   V D L Y Q E V S L S H K D N I I F X P L G I X L X L E M X Q
 13   L N L L K T L G K D N S K N V F E S P M S M S C A L A M V Y
  2   - - - - - - - - - - - - - - - - - - - - - - - - - - - - -

X G A K G X X X X X X X X X Q X L X X X X X X X X X G X X X X - - X  Majority
            |         |         |         |
            70        80        90
 61   L G A K G K A Q Q X X R Q T L Q Q Q E X S A G E E F L C X E
 43   M G A K G N T A A Q M A Q I L S F N K S G G G G D I H - - Q
  2   - - - - - - - - - - - - - - - - - - - - - - - - - - - - -

X X X S L X X X X X X X X X X X X X L X X X X - - - - - - - -  Majority
            |         |         |         |
            100       110       120
 91   V I F S L P S Q R K N K N L H L I L P M P S T X Q E G F T V
 71   G F Q S L L T E V N K T G T Q Y L L R V A N R - - - - - - -
  2   - - - - - - - - - - - - - - - - - - - - - - - - - - - - -
```

FIGURE 2A

```
- - - - - - - - - - - - - - - - - - - - - - - - - L X G X X X X - - - - - - - - - - - - - - - - - - - - - - - - - - - X Q X X X X   Majority
                                                  130                            140                               150
121   K E Q Y L H G N K E X - - - - - - - - - - - - F Q S A I K    222689.ami
 94   - - L F G E K S C D F L S S F R D S C Q K F Y Q A E M E     g464490.PTI6_HUMAN
  2   - - - - - - - - - - - - - - - - - - - - - - - - - - - -    g510193.RNSERPIN_1

X X D F X X X A - X X X X X X I X T W V X X K T X G K I X X X   Majority
                      160                        170                       180
138   L V D F Q D A - K A C A G M I S T W V E R K T D G K I K D M    222689.ami
120   E L D F I S A V E K S R K H I N T W V A E K T E G K I A E L    g464490.PTI6_HUMAN
  2   - - - - - - - - - - - - - - - - - - - - - - - - - - - -      g510193.RNSERPIN_1

X S X X X X X P L T R L V L V N A X Y F X G X W X X X X F X X   Majority
                      190                        200                       210
167   F S G E E F G P L T R L V L V N A I Y F K G D W K Q K F R K    222689.ami
150   L S P G S V D P L T R L V L V N A V Y F R G N W D G Q E D K    g464490.PTI6_HUMAN
  2   - - - - - - - - - - - - - - - - - - - - - - - - - - - -      g510193.RNSERPIN_1

E X T X - - L X X X X X X X X X V X X X X X M K A L L R X X   Majority
                      220                        230                       240
197   E D T Q - - L I N F T K K N G S T V K I P M M K A L L R T K    222689.ami
180   E N T E E R L F K V S K N E E K P V Q M M F K Q S T F K K T    g464490.PTI6_HUMAN
  2   - - - - - - - - - - - - - - - - - - - - - - M K A L L R A K   g510193.RNSERPIN_1
```

```
         YGYFSESSXXXYQVLELPYKGDEFSLIIXLP  Majority
                  250              260               270

225  YGYFSESSLNYQVLELSYKGDEFSLIIILP  222689.ami
210  Y - - - IGEIFTQILVLPYVGKELNMIIMLP  g464490. PTI6_HUMAN
10   YGYFSESSMTYQVLELPYKADEFSLVILLP  g510193.RNSERPIN_1

XEXXDIEEVEKXXTAXXXKW - - LSEMXEE  Majority
                  280              290              300

255  AEGMDIEEVEKLITAQQILKW - - LSEMQEE  222689.ami
236  DETTDLRTVEKELTYEKFVEWTRLDMMDEE  g464490. PTI6_HUMAN
40   TEDVNIEEVEKQVTARHVQKW - - FSELHEE  g510193.RNSERPIN_1

EVEVSLPRFKXXEQKXDFKXVLFSLNXTEIF  Majority
                  310              320              330

283  EVEISLPRFKVEQKVDFKDVLFSLNITEIF  222689.ami
266  EVEVSLPRFKLEESYDMESVLRNLGMTDAF  g464490. PTI6_HUMAN
68   EVEVSLPRFKIEQKLDFKEALFSLNVTEIF  g510193.RNSERPIN_1

S - GGCDLSGITDSSELYVSXVXQKVFFEIN  Majority
                  340              350              360

313  S - GGCDLSGITDSSEVYVSQVTQKVFFEIN  222689.ami
296  ELGKADFSGMSQ - TDLSLSKVVHKSFVEVN  g464490. PTI6_HUMAN
98   S - GGCDLSGITDSSELYVSRAMQKVFFEIN  g510193.RNSERPIN_1
```

FIGURE 2C

PANCREAS-DERIVED SERPIN

This application is a division of 08/977,771 filing date Nov. 25, 1997.

FIELD OF THE INVENTION

The present invention is in the field of molecular biology; more particularly, the present invention describes the nucleic acid and amino acid sequences of a novel pancreas-derived serpin.

BACKGROUND OF THE INVENTION
Serpins

Serpins are extracellular, irreversible serine protease inhibitors. As a group, they are defined on the basis of their structural and functional characteristics—high molecular weight, 370–420 amino acid residues, and C-terminal reactive region. Proteins which have been assigned to the serpin family Include the following: α-1 protease inhibitor, α-1-antichymotrypsin, antithrombin III, α-2-antiplasmin, heparin cofactor II, complement C1 inhibitor, plasminogen activator inhibitors 1 and 2, glia derived nexin, protein C inhibitor, rat hepatocyte inhibitors, crmA (a viral serpin which inhibits interleukin 1-β cleavage enzyme), human squamous cell carcinoma antigen (which may modulate the host immune response against tumor cells), human maspin (which seems to function as a tumor supressor; Zou Z et al (1994) Science 263:526–529), lepidopterian protease inhibitor, leukocyte elastase inhibitor (the only known intracellular serpin), and three orthopoxviruses (which may be involved in the regulation of the blood clotting cascade and/or of the complement cascade in the mammalian host).

In addition, a number of proteins with no known inhibitory activity are also categorized as serpins on the basis of strong sequence and structural similarities. They include bird ovalbumin, angiotensinogen, barley protein Z, corticosteroid binding globulin, thyroxine binding globulin, sheep uterine milk protein, pig uteroferrin-associated protein, an endoplasmic reticulum heat-shock protein (which binds strongly to collagen and could act as a chaperone), pigment epithelium-derived factor, and an estrogen-regulated protein from Xenopus.

The signature pattern for the serpins is based on a well conserved pro-phe sequence which is located ten to fifteen residues C-terminal to the reactive site loop (RSL). The serpin consensus pattern is [LIVMFY]-x-[LIVMFYAC]-[DNQ]-[RKHQS]-[PST]-F-[LIVMFY] [LIVMFYC]-x-[LIVMFAH], and P is found In position 6 of the pattern in most serpins.

Serpins are defined and described in Carrell R and Travis J (1985) Trends Biochem Sci 10:20–24; Carrell R et al (1987) Cold Spring Harbor Symp Quant Biol 52:527–535; Huber R and Carrell RW (1989) Biochemistry 28:8951–8966; and Remold-O'Donneel E (1993) FEBS Lett 315:105–108.

Mode of Action

Protease inhibitors form tight complexes with their target proteases. For instance, small molecule Inhibitors such as tetrapeptide keto esters form a covalent bond with the catalytic site of serine proteases and also interact with substrate-binding subsites. For the Kunitz family of protease inhibitors, extended interactions involving the entire substrate binding surface on both sides of the reactive site are utilized.

The region of a serpin which binds to the target protease is an exposed reactive site loop (RSL). In contrast to the above inhibitors, serpins have mobile RSLs. The RSL sequence from P17 to P8 is highly conserved, and small amino acid with side chains are found at positions P9, P10, P11, P12, and P15 in active inhibitors. Sequence divergence in the hinge region is usually associated with conversion of the molecule from an inhibitor to a substrate. In fact, proteolytic cleavage near the reactive site results in profound structural changes. Cleavage of the characteristic serpin P1-P1' bond of α1-proteinase inhibitor results in a separation of about 69 Å between the two residues (Loebermann H et al (1984) J Mol Biol 177:531–556). In addition, the peptide loop from P14–P2 (numbering from the active site P1-P1') is inserted into the middle of the A-sheet. These structural changes are accompanied by pronounced increase in stability to heat- or guanidine-induced denaturation and this change is referred to as the stressed-to-relaxed (S->R) transition. The ability of a serpin to function as an inhibitor may be directly related to its ability to undergo this S->R transition (Bruch M et al (1988) J Biol Chem 263:1662 6–30; Carrell RW et al (1992) Curr Opin Struct Biol 2:438–446). Ovalbumin, a noninhibitor of the serpin family, is unable to undergo this S->R transition.

To determine the role of small amino acids In the hinge region of protease nexin-1, Braxton SM et al (Keystone Symposium, Mar. 11, 1994) replaced glycine at position 331 (P15) with serine, alanine, proline and valine. The $G_{331}$->V mutation was nearly inactive, the $G_{331}$->P was completely inactive, and replacement of $G_{331}$ with S and A had a smaller effect on inhibition. P12 ($A_{334}$>V) and P10 ($A_{336}$->V) mutations also significantly reduced activity. These mutagenesis experiments indicate that a portion of the RSL, up to at least P10, must incorporate into the A-sheet in order for PN-1 to act as an inhibitor, and mutations which hinder this structural transition cause PN-1 to act as a substrate.

Discovery

The serpin molecule which is the subject of this application was identified among the cDNAs of a normal pancreas library. The exocrine pancreas produces an abundance of proteolytic enzymes such as trypsin, chymotrypsin, carboxypeptidase and the serine proteases which split whole and partially-digested proteins into polypeptides and smaller moieties. Several elastases and nucleases are also found in the pancreatic juice. Other digestive enzymes produced by the pancreas include pancreatic amylase which digests carbohydrates, and pancreatic lipase, cholesterol esterase, and phospholipase which hydrolyze lipids and fats.

The four molecules which control pancreatic secretion are acetylcholine and the hormones, gastrin, cholecystokinin (CCK), and secretin. Acetylcholine is released from the parasympathetic vagus and other cholinergic nerve endings, gastrin is secreted by cells of the stomach, and CCK and secretin are secreted by the upper small intestine. The gastrointestinal (GI) hormones are absorbed into the blood and transported to the pancreas where they stimulate the secretion of enzymes and of sodium bicarbonate and water (which wash the pancreatic enzymes into the duodenum).

The endocrine pancreas consists of islets of Langerhans, whose cells are separated from the exocrine lobules and are distributed throughout the pancreas. The endocrine cells of the islets secrete hormones which participate in the metabolism of proteins, carbohydrates, and fats.

The major endocrine cells are α, β, and δ cells; the minor cells are C cells, EC cells, and PP cells. About 15% of the islet cell population are a cells which are located along the periphery of islets and secrete the hormone glucagon. β cells comprise about 70% of the islet cell population, are located around the center of the islets, and secrete the hormone insulin. δ cells comprise about 10% of the population, are located close to α cells and secrete two different hormones, somatostatin and vasoactive intestinal peptide (VIP). C, EC, and PP cells make up the final 5% of the islet cell population. Although the function of C cells is unknown, EC and PP cells secrete seratonin and pancreatic polypeptide, respectively.

Inflammation of the pancreas or pancreatitis may be classified as either acute or chronic by clinical criteria. With treatment, acute pancreatitis can often be cured and normal function restored. Chronic pancreatitis often results in permanent damage. The precise mechanisms which trigger acute inflammation are not understood. However, some causes in the order of their importance are alcohol ingestion, binary tract disease, post-operative trauma, and hereditary pancreatitis. One theory provides that autodigestion, the premature activation of proteolytic enzymes in the pancreas rather than in the duodenum, causes acute pancreatitis. Any number of other factors including endotoxins, exotoxins, viral infections, ischemia, anoxia, and direct trauma may activate the proenzymes. In addition, any internal or external blockage of pancreatic ducts can also cause an accumulation of pancreatic juices in the pancreas resulting cellular damage.

Anatomy, physiology, and diseases of the pancreas are reviewed, inter alia, in Guyton AC (1991) Textbook of Medical Physiology, WB Saunders Co, Philadelphia Pa.; Isselbacher KJ et al (1994) Harrison's Principles of Internal Medicine, McGraw-Hill, New York City; Johnson KE (1991) Histology and Cell Biology, Harwal Publishing, Media Pa.; and The Merck Manual of Diagnosis and Therapy (1992) Merck Research Laboratories, Rahway N.J.

SUMMARY OF THE INVENTION

The subject invention provides a unique nucleotide sequence which encodes a novel pancreas-derived serpin, also known as pds. The new gene, which was identified from Incyte Clone 222689, encodes PDS polypeptide, and represents a new human serine protease inhibitor.

The invention also comprises diagnostic tests for physiologically or pathologically compromised pancreas which include the steps of testing a sample or an extract thereof with pds DNA, fragments or oligomers thereof. Further aspects of the invention include the antisense DNA of pds; cloning or expression vectors containing pds; host cells or organisms transformed with expression vectors containing pds; a method for the production and recovery of purified PDS polypeptide from host cells; purified PDS polypeptide; antibodies to PDS, and pharmacological compounds using PDS.

DESCRIPTION OF THE FIGURES

FIGS. 1A, 1B, 1C and 1D display the nucleotide sequence for pds and the predicted amino acid sequence of PDS polypeptide.

FIGS. 2A, 2B, 2C and 2D show the amino acid alignment of PDS with human and rat serpins. Alignments shown were produced using the multisequence alignment program of DNASTAR software (DNASTAR Inc, Madison Wis.).

DETAILED DESCRIPTION OF THE INVENTION

Definitions

Figure 2D:
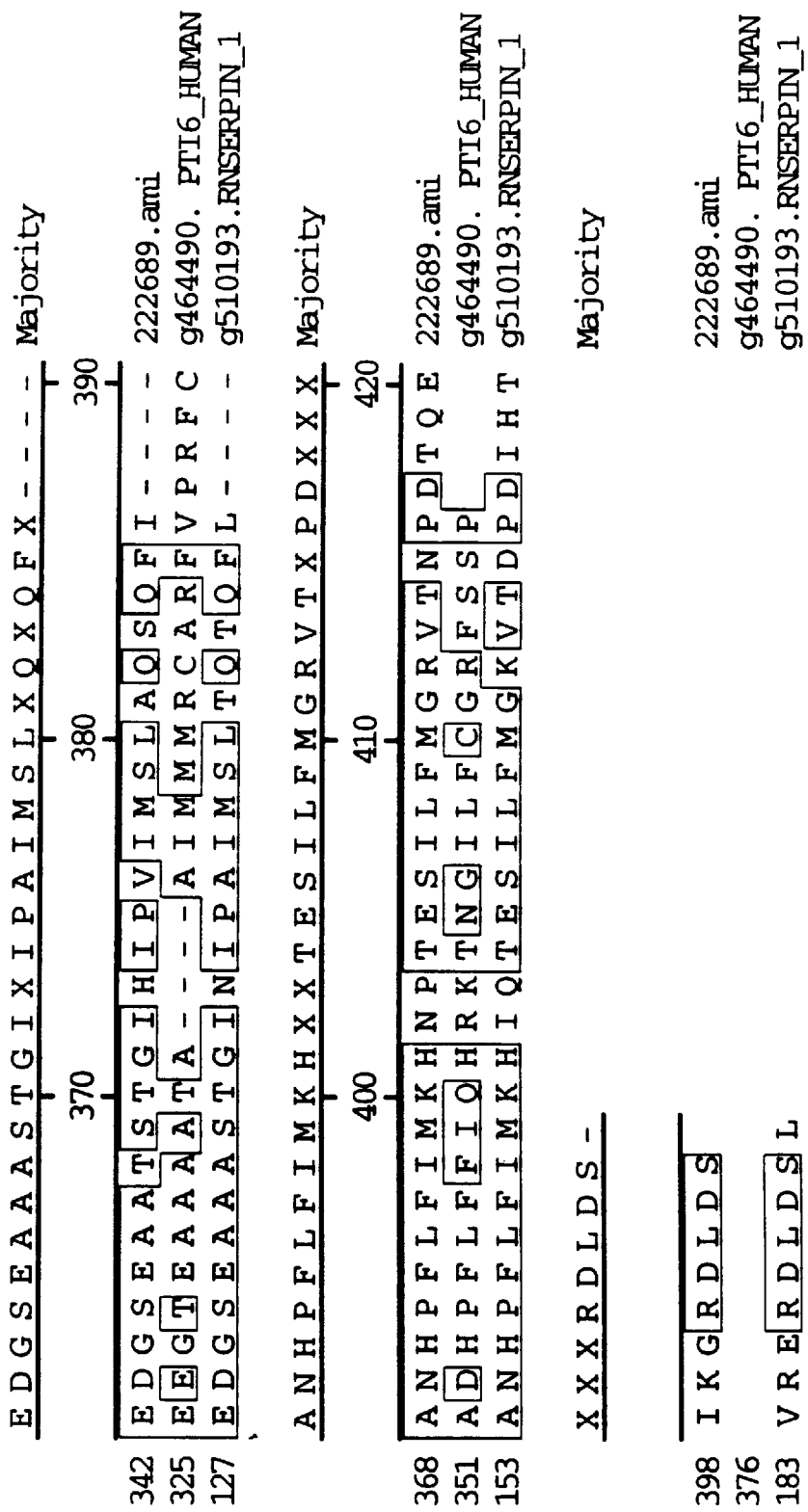

As used herein, pancreas-derived serpin refers to an PDS polypeptide, naturally occurring PDS polypeptide, or active fragments thereof, which are encoded by mRNAs transcribed from the cDNA of Seq ID No 1.

"Active" refers to those forms of PDS which retain biologic and/or immunologic activities of any naturally occurring PDS.

"Naturally occurring PDS" refers to PDS produced by human cells that have not been genetically engineered and specifically contemplates various PDSs arising from post-translational modifications of the polypeptide including but not limited to acetylation, carboxylation, glycosylation, phosphorylation, lipidation and acylation.

"Derivative" refers to polypeptides derived from naturally occurring PDS by chemical modifications such as ubiquitination, labeling (e.g., with radionuclides, various enzymes, etc.), pegylation (derivatization with polyethylene glycol), or by insertion (or substitution by chemical synthesis) of amino acids (aa) such as ornithine, which do not normally occur in human proteins.

"Recombinant variant" refers to any polypeptide differing from naturally occurring PDS by aa insertions, deletions, and substitutions, created using recombinant DNA techniques. Guidance in determining which aa residues may be replaced, added or deleted without abolishing activities of interest, such as cell adhesion and chemotaxis, may be found by comparing the sequence of the particular PDS with that of homologous cathepsins and minimizing the number of aa sequence changes made in regions of high homology.

Preferably, aa "substitutions" are the result of replacing one aa with another aa having similar structural and/or chemical properties, such as the replacement of a leucine with an isoleucine or valine, an aspartate with a glutamate, or a threonine with a serine, i.e., conservative aa replacements. "Insertions" or "deletions" are typically in the range of about 1 to 5 aa. The variation allowed may be experimentally determined by systematically making insertions, deletions, or substitutions of aa in an PDS molecule using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of aa residues of at least about 5 aa, often at least about 7 aa, typically at least about 9 to 13 aa, and, in various embodiments, at least about 17 or more aa. To be active, any PDS polypeptide must have sufficient length to display biologic and/or immunologic activity on their own or when conjugated to a carrier protein such as keyhole limpet hemocyanin.

An "oligonucleotide" or polynucleotide "fragment", "portion," or "segment" is a stretch of nucleotide residues which is long enough to use in polymerase chain reaction (PCR) or various hybridization procedures to amplify or simply reveal related parts of mRNA or DNA molecules. One or both oligonucleotide probes will comprise sequence that is identical or complementary to a portion of PDS where there is little or no identity or complementarity with any known or prior art molecule. The oligonucleotide probes will generally comprise between about 10 nucleotides and 50 nucleotides, and preferably between about 15 nucleotides and about 30 nucleotides.

"Animal" as used herein may be defined to include human, domestic or agricultural (cats, dogs, cows, sheep, etc) or test species (mouse, rat, rabbit, etc).

The present invention includes purified PDS polypeptides from natural or recombinant sources, cells transformed with recombinant nucleic acid molecules encoding PDS. Various methods for the isolation of the PDS polypeptides may be accomplished by procedures well known in the art. For example, such polypeptides may be purified by immunoaffinity chromatography by employing the antibodies provided by the present invention. Various other methods of protein purification well known in the art include those described in Deutscher M (1990) Methods In Enzymology, Vol 182, Academic Press, San Diego Calif.; and Scopes R (1982) Protein Purification: Principles and Practice. Springer-Verlag, New York City, both incorporated herein by reference.

"Recombinant" may also refer to a polynucleotide which encodes PDS and is prepared using recombinant DNA techniques. The DNAs which encode PDS may also include allelic or recombinant variants and mutants thereof.

"Nucleic acid probes" are prepared based on the cDNA sequences which encode PDS provided by the present invention. Nucleic acid probes comprise portions of the sequence having fewer nucleotides than about 6 kb, usually fewer than about 1 kb. After appropriate testing to eliminate false positives, these probes may be used to determine whether mRNAs encoding PDS are present in a cell or tissue or to isolate similar nucleic acid sequences from chromosomal DNA extracted from such cells or tissues as described by Walsh PS et al (1992, PCR Methods Appl 1:241–250).

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, Cold Spring Harbor N.Y.; or Ausubel FM et al (1989) Current Protocols in Molecular Biology, John Wiley & Sons, New York City, both incorporated herein by reference.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, including but not limited to ligand-binding affinities, interchain affinities, or polypeptide degradation or turnover rate. One example involves inserting a stop codon into the nucleotide sequence to limit the size of PDS so as to provide a binding, non-activating ligand of smaller molecular weight which would serve to block the activity of the natural pancreas-derived serpin.

DETAILED DESCRIPTION OF THE INVENTION

The present invention provides a nucleotide sequence identified in Incyte 222689 uniquely identifying a new, pancreas-derived serpin (PDS) of the cysteine protease family which was expressed in pancreatic cells. Because pds is specifically expressed in pancreas, the nucleic acids (pds), polypeptides (PDS) and antibodies to PDS are useful in diagnostic assays for physiologic or pathologic problems of the pancreas. Increased expression of proteases are known to lead to tissue damage or destruction; therefore, a diagnostic test for the presence and expression of PDS can accelerate diagnosis and proper treatment of such problems.

The nucleotide sequence encoding PDS has numerous applications in techniques known to those skilled in the art of molecular biology. These techniques include use as hybridization probes, use in the construction of oligomers for PCR, use for chromosome and gene mapping, use in the recombinant production of PDS, and use in generation of anti-sense DNA or RNA, their chemical analogs and the like. Uses of nucleotides encoding PDS disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, eg, the triplet genetic code, specific base pair interactions, etc.

It will be appreciated by those skilled in the art that as a result of the degeneracy of the genetic code, a multitude of PDS-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring PDS, and all such variations are to be considered as being specifically disclosed.

Although the nucleotide sequences which encode PDS and/or its variants are preferably capable of hybridizing to the nucleotide sequence of naturally occurring PDS under stringent conditions, It may be advantageous to produce nucleotide sequences encoding PDS or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding PDS and/or its derivatives without altering the encoded aa sequence include the production of RNA transcripts having more desirable properties, such as a greater half-life, than transcripts produced from the naturally occurring sequence.

Nucleotide sequences encoding PDS may be joined to a variety of other nucleotide sequences by means of well established recombinant DNA techniques (cf Sambrook J et al. supra). Useful nucleotide sequences for joining to pds include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for pds-specific nucleic acid hybridization probes capable of hybridizing with naturally occurring nucleotide sequences encoding PDS. Such probes may also be used for the detection of similar serpin encoding sequences and should preferably contain at least 50% of the nucleotides from the conserved region or active site. The hybridization probes of the subject invention may be derived from the nucleotide sequences of the SEQ ID NO 1 or from genomic sequences including promoters, enhancer elements and/or possible introns of respective naturally occurring pds molecules. Hybridization probes may be labeled by a variety of reporter groups, including radionuclides such as 32P or 35S, or enzymatic labels such as alkaline phosphatase coupled to the probe via avidin/biotin coupling systems, and the like.

PCR as described U.S. Pat. Nos 4,683,195; 4,800,195; and 4,965,188 provides additional uses for oligonucleotides based upon the nucleotide sequence which encodes PDS. Such probes used in PCR may be of recombinant origin, may be chemically synthesized, or a mixture of both and comprise a discrete nucleotide sequence for diagnostic use or a degenerate pool of possible sequences for identification of closely related genomic sequences.

Other means of producing specific hybridization probes for pds DNAs include the cloning of nucleic acid sequences encoding PDS or PDS derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding PDS and their derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the pds sequences or any portion thereof.

The nucleotide sequence can be used in an assay to detect inflammation or disease associated with abnormal levels of expression of PDS. The nucleotide sequence can be labeled by methods known in the art and added to a fluid or tissue sample from a patient under hybridizing conditions. After an Incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample, and the assay indicates the presence of inflammation and/or disease.

The nucleotide sequence for pancreas-derived serpin can be used to construct hybridization probes for mapping that gene. The nucleotide sequence provided herein may be mapped to a particular chromosome or to specific regions of that chromosome using well known genetic and/or chromosomal mapping techniques. These techniques include in situ hybridization, linkage analysis against known chromosomal markers, hybridization screening with libraries, flow-sorted chromosomal preparations, or artificial chromosome constructions YAC or P1 constructions. The technique of fluorescent in situ hybridization of chromosome spreads has been described, among other places, in Verma et al (1988) Human Chromosomes: A Manual of Basic Techniques, Pergamon Press, New York City.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of pds on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

Nucleotide sequences encoding PDS may be used to produce purified PDS using well known methods of recombinant DNA technology. Among the many publications that teach methods for the expression of genes after they have been isolated is Goeddel (1990) Gene Expression Technology, Methods and Enzymology, Vol 185, Academic Press, San Diego Calif. PDS may be expressed in a variety of host cells, either prokaryotic or eukaryotic. Host cells may be from the same species in which PDS nucleotide sequences are endogenous or from a different species. Advantages of producing PDS by recombinant DNA technology include obtaining adequate amounts of the protein for purification and the availability of simplified purification procedures.

Cells transformed with DNA encoding PDS may be cultured under conditions suitable for the expression of serpins and recovery of the protein from the cell culture. PDS produced by a recombinant cell may be secreted or may be contained intracellularly, depending on the pds sequence and the genetic construction used. In general, it is more convenient to prepare recombinant proteins in secreted form. Purification steps vary with the production process and the particular protein produced.

In addition to recombinant production, fragments of PDS may be produced by direct peptide synthesis using solid-phase techniques (cf Stewart et al (1969) Solid-Phase Peptide Synthesis, WH Freeman Co, San Francisco Calif.; Merrifield J (1963) J Am Chem Soc 85:2149–2154. In vitro protein synthesis may be performed using manual techniques or by automation. Automated synthesis may be achieved, for example, using Applied Biosystems 431A Peptide Synthesizer (Foster City, California Calif.) in accordance with the instructions provided by the manufacturer. Various fragments of PDS may be chemically synthesized separately and combined using chemical methods to produce the full length molecule.

PDS for antibody induction does not require biological activity; however, the protein must be immunogenic. Peptides used to induce specific antibodies may have an aa sequence consisting of at least five aa, preferably at least 10 aa. They should mimic a portion of the aa sequence of the protein and may contain the entire aa sequence of a small naturally occurring molecule such as PDS. Short stretches of PDS aa may be fused with those of another protein such as keyhole limpet hemocyanin and the chimeric molecule used for antibody production.

Antibodies specific for PDS may be produced by inoculation of an appropriate animal with the polypeptide or an antigenic fragment. An antibody is specific for PDS if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–3837, or Huse WD et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding PDSs.

An additional embodiment of the subject invention is the use of PDS as a specific protease inhibitor to treat viral infections, endotoxin or exotoxin poisoning, ischemia, anoxia, direct trauma, and similar physiologic or pathologic problems of the pancreas.

PDS as a bioactive agent or composition may be administered in a suitable therapeutic dose determined by any of several methodologies Including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It Is contemplated that the therapeutic, bioactive composition may be delivered by intravenous infusion into the bloodstream or any other effective means which could be used for treating problems involving excess expression and activity of proteases.

The examples below are provided to illustrate the subject invention. These examples are provided by way of illustration and are not included for the purpose of limiting the invention.

EXAMPLES

Isolation of mRNA and Construction of cDNA Libraries

The pds sequence was identified among the sequences comprising the human pancreas library of U.S. patent application Ser. No. 08/393,220. The normal pancreas used for this library was obtained from the Keystone Skin Bank, International Institute for the Advancement of Medicine (Exton Pa.). Normal pancreas tissue from a 56 year old Caucasian male (Lot HDS330) was flash frozen, ground in a mortar and pestle, and lyzed immediately in buffer containing guanidinium isothiocyanate. Lysis was followed by several phenol chloroform extractions and ethanol precipitation. Poly A+ RNA was isolated using biotinylated oligo d(T) primer and streptavidin coupled to a paramagnetic particle (Promega Corp, Madison Wis.) and sent to Stratagene (La Jolla Calif.).

Stratagene prepared the cDNA library using oligo d(T) priming. Synthetic adapter oligonucleotides were ligated onto the cDNA molecules enabling them to be inserted into the Uni-ZAP™ vector system (Stratagene). This allowed high efficiency unidirectional (sense orientation) lambda library construction and the convenience of a plasmid system with blue/white color selection to detect clones with cDNA insertions.

The quality of the cDNA library was screened using DNA probes, and then, the pBluescript® phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into *E. coli* host strain XL1-Blue® (Stratagene). The high transformation efficiency of this bacterial strain increases the probability that the cDNA library will contain rare, underrepresented clones. Alternative unidirectional vectors might include, but are not limited to, pcDNAI (Invitrogen, San Diego Calif.) and pSHlox-1 (Novagen, Madison Wis.).

Isolation of cDNA Clones

The phagemid forms of Individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and create a smaller, single-stranded circular phagemid DNA molecule that includes all DNA sequences of the pBluescript plasmid and the cDNA insert. The phagemid DNA was released from the cells and purified, then used to reinfect fresh bacterial host cells (SOLR, Stratagene Inc), where the double-stranded phagemid DNA was produced. Because the phagemid carries the gene for β-lactamase, the newly transformed bacteria were selected on medium containing ampicillin.

Phagemid DNA was purified using the QIAWELL-8 Plasmid Purification System from QIAGEN® DNA Purification System (QIAGEN Inc, Chatsworth Calif.). This technique provides a rapid and reliable high-throughput method for lysing the bacterial cells and isolating highly purified phagemid DNA. The DNA eluted from the purification resin was suitable for DNA sequencing and other analytical manipulations.

An alternate method of purifying phagemid has recently become available. It utilizes the Miniprep Kit (Catalog No. 77468, available from Advanced Genetic Technologies Corporation, Gaithersburg Md.). This kit is in the 96-well format and provides enough reagents for 960 purifications. Each kit is provided with a recommended protocol, which has been employed except for the following changes. First, the 96 wells are each filled with only 1 ml of sterile terrific broth with carbenicillin at 25 mg/L and glycerol at 0.4%. After the wells are inoculated, the bacteria are cultured for 24 hours and lysed with 60 µl of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block for storage.

Sequencing of cDNA Clones

The cDNA inserts from random isolates of the pancreas library were sequenced in part. Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the Applied Biosystems 377 or 373 -DNA sequencer).

Homology Searching of cDNA Clones and Deduced Proteins

Each sequence so obtained was compared to sequences in GenBank using a search algorithm developed by Applied Biosystems Inc. and incorporated into the INHERIT™ 670 Sequence Analysis System. In this algorithm, Pattern Specification Language (developed by TRW Inc.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments of the protein sequence were used to display the results of the homology search.

Peptide and protein sequence homologies were ascertained using the INHERIT 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul SF (1993) J Mol Evol 36:290–300; Altschul, SF et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologues. Although it is ideal for matches which do not contain gaps, it is inappropriate for performing motif-style searching. The fundamental unit of BLAST algorithm output is the high-scoring segment pair (HSP).

An HSP consists of two sequence fragments of arbitrary but equal lengths whose alignment Is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

The nucleotide sequence for the entire coding region of the pancreas-derived serpin, PDS, claimed in this invention is shown in FIGS. 1A, 1B, 1C, and 1D.

Identification and Full Length Sequencing of the Genes

From all of the randomly picked and sequenced clones of the pancreas library, the PDS sequence was homologous to but clearly different from any known serpin. The complete nucleotide sequence was obtained using Gene Amp XL PCR™ (Perkin Elmer, Foster City Calif.) and oligonucleotides designed from Incyte 222689 to extend the serpin sequence to its full length.

The sequence for the full length pancreas-derived serpin was translated, and the in-frame translation is shown in FIGS. 1A, 1B, 1C, and 1D. When all three possible predicted translations of the sequence were searched against protein databases such as SwissProt and PIR, no exact matches were found to the possible translations of PDS. FIGS. 2A, 2B, 2C and 2D shows the comparison of the PDS amino acid sequence with GenBank human and rat serpins. The substantial regions of homology among these molecules begin at $M_{218}$. The rat serpin with the closest homology and from which the new serpin was identified is missing the first 217 residues. Other diagnostic residues are: 1) P15 which is $G_{247}$, 2) P1 which is $M_{382}$, and 3) P1' is $S_{363}$. It should be noted that PDS has an extra amino acid between P1 and P15. Further analysis of this molecule suggests that It is specific for chymotrypsin-like proteases which cleave their target proteins after hydrophobic residues.

Antisense analysis

Knowledge of the cDNA sequence of the new serpin gene will enable its use in antisense technology in the investigation of gene function. Oligonucleotides, genomic or cDNA fragments comprising the antisense strand of PDS can be used either in vitro or in vivo to inhibit expression of the protein. Such technology is now well known in the art, and probes can be designed at various locations along the nucleotide sequence. By treatment of cells or whole test animals with such antisense sequences, the gene of interest can effectively be turned off. Frequently, the function of the gene can be ascertained by observing behavior at the cellular, tissue or organismal level (e.g. lethality, loss of differentiated function, changes in-morphology, etc).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

Expression of PDS

Expression of PDS may be accomplished by subcloning the cDNAs into appropriate expression vectors and transfecting the vectors into appropriate expression hosts. In this particular case, the cloning vector used in the generation of the full length clone also provides for direct expression of the included pds sequence in E coli. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the Isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The pds cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced PDS can be recovered from the conditioned medium and analyzed using chromatographic methods known in the art.

Isolation of Recombinant PDS

PDS may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on Immobilized immunoglobulin, and the domain utilized in the FLAGS extension/affinity purification system (Immunex Corp., Seattle Wash.). The inclusion of a cleavable linker sequence such as Factor XA or enterokinase (Invitrogen, San Diego Calif.) between the purification domain and the pds sequence may be useful to facilitate expression of PDS.

Production of PDS Specific Antibodies

Two approaches are utilized to raise antibodies to PDS, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of PDS, as deduced from translation of the cDNA, is analyzed to determine regions of high immunogenicity. Oligopeptides comprising appropriate hydrophilic regions, as shown in FIG. 3, are synthesized and used in suitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled PDS to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled PDS, 1 mg/ml. Clones producing antibodies will bind a quantity of labeled PDS which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least 10e8 Me-1, preferably 10e9 to 10e10 or stronger, will typically be made by standard procedures as described in Harlow and Lane (1988) Antibodies: A Laboratory Manual. Cold Spring Harbor Laboratory, Cold Spring Harbor N.Y.; and in Goding (1986) Monoclonal Antibodies: Principles and Practice, Academic Press, New York City, both incorporated herein by reference.

Diagnostic Test Using PDS Specific Antibodies

Particular PDS antibodies are useful for the diagnosis of prepathologic conditions, and chronic or acute diseases which are characterized by differences in the amount or distribution of PDS. To date, PDS has only been expressed in the pancreas library and is thus specific for the normal, abnormal or pathological function of the pancreas.

Diagnostic tests for PDS include methods utilizing the antibody and a label to detect PDS in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound PDS, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on PDS is preferred, but a competitive binding assay may be employed. These assays are described, among other places, in Maddox, DE et al (1983, J Exp Med 158:1211).

Purification of Native PDS Using Specific Antibodies

Native or recombinant PDS can be purified by immunoaffinity chromatography using antibodies specific for PDS. In general, an immunoaffinity column is constructed by covalently coupling the anti-PDS antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of PDS by preparing a fraction from cells containing PDS in a soluble form. This preparation is derived by solubilization of the whole cell or of a subcellular fraction obtained via differential centrifugation by the addition of detergent or by other methods well known in the art. Alternatively, soluble PDS containing a signal sequence may be secreted in useful quantity into the medium in which the cells are grown.

A soluble PDS-containing preparation is passed over the immunoaffinity column, and the column is washed under conditions that allow the preferential absorbance of serpin (eg, high ionic strength buffers in the presence of detergent). Then, the column is eluted under conditions that disrupt antibody/PDS binding (e.g., a buffer of pH 2–3 or a high concentration of a chaotrope such as urea or thiocyanate ion), and PDS is collected.

PDS Activity

The activity of purified or expressed PDS may be tested by mixing a known quantity of the enzyme with a potential substrate protease such as chymostrypsin and a purified protein which chymostrypsin usually cleaves. The ability of a given amount of PDS to inhibit chymotrypsin can be assayed by FPLC of the protein fragments produced under a given set of conditions in a specific period of time.

Alternatively, running a sample of the reaction materials on a nondenaturing gel shows the protease inhibitor complex, protease, inhibitor, protein substrate and protein fragments as different sized peptides.

Rational Drug Design

The goal of rational drug design is to produce structural analogs of biologically active polypeptides of interest or of small molecules with which they interact, eg, agonists, antagonists, etc. Any of these examples can be used to fashion drugs which are more active or stable forms of the polypeptide or which enhance or interfere with the function of a polypeptide in vivo (cf Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous serpin-like molecules or to identify efficient inhibitors. Useful examples of rational drug design may include molecules which have improved activity or stability as shown by Braxton S and Wells JA (1992 Biochemistry 31:7796–7801) or which act as inhibitors, agonists, or antagonists of native peptides as shown by Athauda SB et al (1993 J Biochem 113:742–746), incorporated herein by reference.

It is also possible to Isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the PDS amino acid sequence provided herein will provide guidance to those employing computer modeling techniques in place of or in addition to x-ray crystallography.

Use and Administration of PDS

Since PDS is an inhibitor, it may be used to treat excessive protease production. PDS will be formulated in a nontoxic, inert, pharmaceutically acceptable aqueous carrier medium (PDS treatment, PDST) preferably at a pH of about 5 to 8, more preferably 6 to 8, although the pH may vary according to the characteristics of the formulation and its administration. Characteristics such as solubility of the molecule, half-life and antigenicity/immuno-genicity will aid in defining an effective carrier. Native human proteins are preferred as PDST, but recombinant, organic or synthetic molecules resulting from drug design may be equally effective in particular situations.

PDSTs may be delivered by known routes of administration including but not limited to topical creams and gels; transmucosal spray and aerosol, transdermal patch and bandage; injectable, intravenous and lavage formulations; and orally administered liquids and pills, particularly formulated to resist stomach acid and enzymes. The particular formulation, exact dosage, and route of administration will be determined by the attending physician and will vary according to each specific situation.

Such determinations are made by considering multiple variables such as the condition to be treated, the PDST to be administered, and the pharmacokinetic profile of the particular PDST. Additional factors which may be taken into account include disease state (e.g. severity) of the patient, age, weight, gender, diet, time of administration, drug combination, reaction sensitivities, and tolerance/response to therapy. Long acting PDST formulations might be administered every 3 to 4 days, every week, or once every two weeks depending on half-life and clearance rate of the particular PDST.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225;212. It is anticipated that different formulations will be effective for different uses of PDST and that administration targeting a tissue or organ may necessitate delivery in a specific manner.

It is contemplated that pancreatitis or other conditions or diseases of the pancreas caused by viral infections, endotoxin or exotoxin poisoning, ischemia, anoxia, and direct trauma which may cause the overexpression of proteases may be treated with PDSTs.

All publications and patents mentioned in the above specification are herein incorporated by reference. The foregoing written specification is considered to be sufficient to enable one skilled in the art to practice the invention. Indeed, various modifications of the above described modes for carrying out the invention which are readily apparent to those skilled in the field of molecular biology or related fields are intended to be within the scope of the following claims.

What is claimed is:

1. A purified pancreas-derived serpin polypeptide comprising the amino acid sequence of SEQ ID NO 2.

2. An antibody which specifically binds the polypeptide of claim 1.

3. A method of detecting a disease which is associated with altered expression of PDS comprising the steps of:
   a) providing a biological sample; and
   b) combining the biological sample with the antibody of claim 2.

4. A method for using a protein to screen a library of other molecules for a molecule which specifically binds the protein, the method comprising:
   (a) combining the protein of claim 1 with the library of molecules under conditions suitable to allow complex formation, and
   (b) detecting complex formation, wherein the presence of the complex identifies a molecule which specifically binds the protein.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1221 base pairs
      (B) TYPE: nucleic acid
      (C) STRANDEDNESS: single
      (D) TOPOLOGY: linear (ii) MOLECULE TYPE: protein (vii) IMMEDIATE SOURCE:
      (A) LIBRARY: Pancreas
      (B) CLONE: 222689

(ix) FEATURE:
      (A) NAME/KEY: CDS
      (B) LOCATION: 1..1221

(xi) SEQUENCE DESCRIPTION: SEQ ID NO:1:

```
ATGGACACAA TCTTCGNGTG GAGTCTTCTA TTGCTGTTTN GGGGNAGTCA AGCCTCAAGA      60

TGCTCAGCTC AAAAAAATAC CGAATTTGGA GTGGATCTTT ATCAAGAGGT TTCCTTGTCT     120

CATAAGGACA ACATTATTTT TNCACCCCTT GGAATANCTT TGGNTCTCGA GATGGNACAA     180

CTGGGAGCCA AAGGAAAAGC ACAGCAGNAG NTAAGACAAA CTTTACAACA ACAGGAANCC     240

TCAGCTGGGG AAGAATTTCT TTGTNCTGAA GTCATTTTCT CTCTGCCATC TCAGAGAAAA     300

AACAAGAATT TACATTTAAT CTTGCCAATG CCCTCTACCT NTCAAGAAGG ATTCACTGTG     360

AAAGAACAGT ATCTCCATGG CAACAAGGAA TNTTTTCAGA GTGCTATAAA ACTGGTGGAT     420

TTTCAAGATG CAAAGGCTTG TGCAGGGATG ATAAGTACCT GGGTAGAAAG AAAAACAGAT     480

GGAAAAATTA AAGACATGTT TTCAGGGGAA GAATTTGGCC CTCTGACTCG GCTTGTCCTG     540

GTGAATGCTA TTTATTTCAA AGGAGATTGG AAACAGAAAT TCAGAAAAGA GGACACACAG     600

CTGATAAATT TTACTAAGAA AAATGGTTCA ACTGTCAAAA TTCCAATGAT GAAGGCTCTT     660

CTGAGAACAA AATATGGTTA TTTTTCTGAA TCTTCCCTGA ACTACCAAGT TTTAGAATTG     720
```

-continued

```
TCTTACAAAG GTGATGAATT TAGCTTAATT ATCATACTTC CTGCAGAAGG TATGGATATA      780

GAAGAAGTGG AAAAACTAAT TACTGCTCAA CAAATCCTAA AATGGCTCTC TGAGATGCAA      840

GAAGAGGAAG TAGAAATAAG CCTCCCTAGA TTTAAAGTAG AACAAAAAGT AGACTTCAAA      900

GACGTTTTGT TTTCTTTGAA CATAACCGAG ATATTTAGTG GTGGCTGCGA CCTTTCTGGA      960

ATAACAGATT CTTCTGAAGT GTATGTTTCC CAAGTGACGC AAAAAGTTTT CTTTGAGATA     1020

AATGAAGATG GTAGTGAAGC TGCAACATCA ACTGGCATAC ACATCCCTGT GATCATGAGT     1080

CTGGCTCAAA GCCAATTTAT AGCAAATCAT CCATTTCTGT TTATTATGAA GCATAACCCA     1140

ACAGAATCAA TTCTGTTTAT GGGAAGAGTG ACAAATCCTG ACACCCAGGA GATAAAAGGA     1200

AGAGATTTAG ATTCACTGTG A                                               1221
```

(2) INFORMATION FOR SEQ ID NO:2:

(i) SEQUENCE CHARACTERISTICS:
        (A) LENGTH: 406 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Thr Ile Phe Xaa Trp Ser Leu Leu Leu Phe Xaa Gly Ser
 1               5                  10                  15

Gln Ala Ser Arg Cys Ser Ala Gln Lys Asn Thr Glu Phe Gly Val Asp
                20                  25                  30

Leu Tyr Gln Glu Val Ser Leu Ser His Lys Asp Asn Ile Ile Phe Xaa
            35                  40                  45

Pro Leu Gly Ile Xaa Leu Xaa Leu Glu Met Xaa Gln Leu Gly Ala Lys
        50                  55                  60

Gly Lys Ala Gln Gln Xaa Xaa Arg Gln Thr Leu Gln Gln Gln Glu Xaa
 65                  70                  75                  80

Ser Ala Gly Glu Glu Phe Leu Cys Xaa Glu Val Ile Phe Ser Leu Pro
                85                  90                  95

Ser Gln Arg Lys Asn Lys Asn Leu His Leu Ile Leu Pro Met Pro Ser
            100                 105                 110

Thr Xaa Gln Glu Gly Phe Thr Val Lys Glu Gln Tyr Leu His Gly Asn
        115                 120                 125

Lys Glu Xaa Phe Gln Ser Ala Ile Lys Leu Val Asp Phe Gln Asp Ala
    130                 135                 140

Lys Ala Cys Ala Gly Met Ile Ser Thr Trp Val Glu Arg Lys Thr Asp
145                 150                 155                 160

Gly Lys Ile Lys Asp Met Phe Ser Gly Glu Glu Phe Gly Pro Leu Thr
                165                 170                 175

Arg Leu Val Leu Val Asn Ala Ile Tyr Phe Lys Gly Asp Trp Lys Gln
            180                 185                 190

Lys Phe Arg Lys Glu Asp Thr Gln Leu Ile Asn Phe Thr Lys Lys Asn
        195                 200                 205

Gly Ser Thr Val Lys Ile Pro Met Met Lys Ala Leu Leu Arg Thr Lys
    210                 215                 220

Tyr Gly Tyr Phe Ser Glu Ser Ser Leu Asn Tyr Gln Val Leu Glu Leu
225                 230                 235                 240

Ser Tyr Lys Gly Asp Glu Phe Ser Leu Ile Ile Ile Leu Pro Ala Glu
                245                 250                 255

Gly Met Asp Ile Glu Glu Val Glu Lys Leu Ile Thr Ala Gln Gln Ile
```

-continued

```
                    260                    265                       270
Leu Lys Trp Leu Ser Glu Met Gln Glu Glu Glu Val Glu Ile Ser Leu
        275                    280                   285
Pro Arg Phe Lys Val Glu Gln Lys Val Asp Phe Lys Asp Val Leu Phe
    290                    295                   300
Ser Leu Asn Ile Thr Glu Ile Phe Ser Gly Gly Cys Asp Leu Ser Gly
305                    310                   315                   320
Ile Thr Asp Ser Ser Glu Val Tyr Val Ser Gln Val Thr Gln Lys Val
                325                    330                   335
Phe Phe Glu Ile Asn Glu Asp Gly Ser Glu Ala Ala Thr Ser Thr Gly
                340                    345                   350
Ile His Ile Pro Val Ile Met Ser Leu Ala Gln Ser Gln Phe Ile Ala
            355                    360                   365
Asn His Pro Phe Leu Phe Ile Met Lys His Asn Pro Thr Glu Ser Ile
        370                    375                   380
Leu Phe Met Gly Arg Val Thr Asn Pro Asp Thr Gln Glu Ile Lys Gly
385                    390                    395                   400
Arg Asp Leu Asp Ser Leu
                405
```